United States Patent
Li (10) Patent No.: US 7,291,600 B2
(45) Date of Patent: Nov. 6, 2007

(54) NON-T CELL BINDING PEPTIDES AND THEIR USES

(76) Inventor: Zhanguo Li, Department of Rheumatology, People's Hospital, 11 Xizhimen South Street, Xicheng District, Beijing (CN) 100044

( * ) Notice: Subject to any disclaimer, the term of this patent is extended or adjusted under 35 U.S.C. 154(b) by 0 days.

(21) Appl. No.: 10/519,524

(22) PCT Filed: Jun. 26, 2003

(86) PCT No.: PCT/CN03/00496

§ 371 (c)(1),
(2), (4) Date: Dec. 27, 2004

(87) PCT Pub. No.: WO2004/003007

PCT Pub. Date: Jan. 8, 2004

(65) Prior Publication Data

US 2006/0166890 A1    Jul. 27, 2006

(30) Foreign Application Priority Data

Jun. 27, 2002    (CN)    ................................ 02 1 23412

(51) Int. Cl.
*A61K 38/08*    (2006.01)
*C07K 7/06*    (2006.01)

(52) U.S. Cl. ........................................ 514/15; 530/328
(58) Field of Classification Search .................... None
See application file for complete search history.

(56) References Cited

U.S. PATENT DOCUMENTS

2002/0037844 A1    3/2002    Myers et al.

FOREIGN PATENT DOCUMENTS

| CN | 1183784 | 6/1998 |
| CN | 1310724 | 8/2001 |
| WO | WO96/41644 A1 | 12/1996 |
| WO | WO98/33811 A1 | 8/1998 |

OTHER PUBLICATIONS

Andersson et al. Definition of MHC and T cell receptor contacts ... Proceedings of the National Academy of Sciences USA. Jun. 1998, vol. 95, pp. 7574-7579.*

* cited by examiner

*Primary Examiner*—Jeffrey Edwin Russel
(74) *Attorney, Agent, or Firm*—Gordon & Rees LLP (57) ABSTRACT

The present invention provides a non-T cell binding peptide and its analogs used for the treatment of rheumatoid arthritis. The polypeptide therapeutic agent can specifically inhibit abnormal immune responses of the rheumatoid arthritis, and fundamentally control the progression of this disease with effect on the initiating factor of the disease development.

6 Claims, 5 Drawing Sheets

NON-T CELL BINDING PEPTIDES AND THEIR USES

CROSS REFERENCES TO RELATED APPLICATIONS

This application is the U.S. National Stage filing of PCT/CN03/00496 which claims the benefit of priority of Chinese patent application Ser. No. CN02123412.4, filed Jun. 27, 2002.

FIELD OF THE INVENTION

The present invention relates to the preparation of non-T cell binding peptides and their uses as drugs for the treatment of rheumatoid arthritis and other autoimmune diseases.

BACKGROUND

Rheumatoid arthritis (RA) is a kind of chronic autoimmune disease mainly characterized by joint destruction and deformity, which can disable patients. With the morbidity of 0.34% in China, there are nearly five million patients in the whole country, and the percentage of disability reaches up to 93%. The procedure of the onset of the disease is an "initiation—linked immune response" procedure driven by antigens. Immune damage(s) mediated by infection factor(s) and autoimmune response(s) are the basis for the onset and progression of rheumatoid arthritis. Antigen polypeptides are expressed through antigen presenting cells in vivo, and they activate T lymphocyte, which results in the release of cytokines and the increase of production of inflammatory factors, such as immune globulins, chemokines and free radicals, which consequently induce typical pathologic changes of rheumatoid arthritis, including vasculitis, synovium hyperplasia, damage(s) of cartilages and bones.

Currently, there is still no drug which can completely control rheumatoid arthritis. Generally, non-steroidal anti-inflammatory drugs such as Brufen and declofenic acid are used clinically for temporarily relieving symptoms. Disease-modifying anti-rheumatoid drugs, such as methotrexate and leflunomide, are used to extensively inhibit immune responses by suppressing DNA synthesis and thereby inhibit joint inflammation. Therefore, such drugs do not take effect on the initial procedure of the disease onset in the treatment of rheumatoid arthritis, and it is very difficult for them to control the disease completely, which results in the continuous progress of the systemic and joint damages, and disability at last. Moreover, because of the extensive immune suppression of these drugs, there are a lot of side effects, such as myelosuppression and abnormal hepatic functions, and therefore these drugs cannot be administered to many patients.

At present, there is an urgent need for drugs which can take effect on the etiology of rheumatoid arthritis and treat this disease by suppressing the initial procedure of immune responses. Thus after many years of research, the inventors found the non-T cell binding peptides, which can be used for treating rheumatoid arthritis. It proves in our research that the peptides of the present invention can inhibit the recognition to antigens of HLA-DRβ1 molecules and T cells, and thereby inhibit the consequent autoimmune responses. As such, they can prevent and control the onset and development of the disease through the key procedure of the onset of rheumatoid arthritis.

SUMMARY OF THE INVENTION

One object of the present invention is to provide a non-T cell binding peptide, which can be used to treat rheumatoid arthritis effectively.

Another object of the present invention is to provide the use of said non-T cell binding peptide in the treatment of rheumatoid arthritis.

Finally, the present invention provides a pharmaceutical composition(s) comprising the said non-T cell binding peptide.

The term "non-T cell binding peptide" used herein refers to the peptides which are produced by altering one or more amino acids of SEQ ID NOs: 1-7 and which can still bind to HLA-DRβ1 after alteration. The methods for altering amino acid sequences are well known in the art.

Generally, the present invention includes: one or more amino acid sequences which can bind to T cell receptor and which can stimulate T cell proliferation in wild type CII peptide are substituted with Alanine (A) or Glycine (G), and the amino acids which can bind to HLA-DRβ1 are remained, thus producing a group of novel CII polypeptide molecules which can only bind to HLA-DRβ1 molecules and cannot be recognized by T cell receptors, i.e., the seven non-T cell binding peptides listed in the attachment (267A, 268A, 269A, 270A, Mut 269-270, Mut 268-270, Mut 267-270). Their specific sequences and IDs are shown in the Sequence Listing section.

The recognition and binding to each other among the three molecules. HLA-DRβ1, antigen peptide and T cell receptor, is the key procedure of abnormal immune responses in rheumatoid arthritis. Therefore, the object of the present invention is to block the binding of T cell(s) to antigen(s), which is the key point of the etiology of rheumatoid arthritis, and suppress the in vivo abnormal immune responses in patients with rheumatoid arthritis by utilizing the recognition of T cells to antigens and the competitive inhibition of non-T cell binding peptides to pathogenic antigens, and thereby control the progress of onset and development of the disease so as to reach the goal of treating rheumatoid arthritis completely.

It proves that amino acids 70-74 in HLA-DRβ1 contain a consensus sequence of QKRAA (SEQ ID NO:9) or QRRAA (SEQ ID NO:10) (i.e. Gln-Lys/Arg-Arg-Ala-Ala, glutamine-lysine/arginine-arginine-alanine-alanine)[1]. This consensus sequence is related to the formation of HLA-DRβ1-antigen binding cleft and is the functional amino acids which function in the binding to antigens. Plenty of research by the inventors and Wucherfennig et al. proved that positively charged amino acid 71 (Lys or Arg) in this sequences is the key site of antigen binding [2-8].

By research on crystal structure of HLA-DRβ1-antigen dimer using X-ray diffraction technique, it is found that a variety of antigen peptides which bind to rheumatoid arthritis related to HLA-DRβ1 (DR4/DR1) molecules are extremely similar in configuration, including denatured type II collagen (CII) and Heat Shock Protein (HSP)[9-2]. From the 3-dimentional structures of these peptides (FIG. 1), it can be seen that the side chains of Phe263 (P1), Glu 266 (P4) and Gly271 (P9) stretch to the HLA-DRβ1 molecule in the left, and are imbedded into the antigen binding cleft entirely or partially, while side chains of the other amino acids stretch to another side of the side opposite to HLA-DRβ1 (the side of T cell receptor) to stimulate T cell activation. From FIG. 2, it can be seen that the side chains of P1, P4, and P9 of CII polypeptide are imbedded into the antigen binding "pocket" of HLA-DRβ1. Negatively charged P4 (Glu) is adjacent to positively charged amino acid 71 (Lys71) of HLA-DRβ1, which forms the polar binding with high affinity. Therefore, Glu 263, Gly265, Gly 266, Gly 271, and Glu 272 and thus activates T cells. From this we can see that the major HLA-DRβ1 binding amino acids in CII polypeptide are Phe 262, Gly265, Gly266, Gly 271, and Glu 272, whilst the major T cell receptor (TCR) binding amino acids are Gln 267, Gly 268, Pro 269 and Lys 270 (Table 1).

TABLE 1

Amino acids binding to T cell receptors and HLA-DRβ1 in CII (SEQ ID NO:8)

| | | | | | | | | | |
|---|---|---|---|---|---|---|---|---|---|
| DRβ1 | | DRβ1 | DRβ1 | | | | | DRβ1 | DRβ1 |
| ↑ | | ↑ | ↑ | | | | | ↑ | ↑ |
| F | K | G | E | Q | G | P | K | G | E |
| 263 | 264 | 265 | 266 | 267 | 268 | 269 | 270 | 271 | 272 |
| | | | | ↓ | ↓ | ↓ | ↓ | | |
| | | | | TCR | TCR | TCR | TCR | | |

* F = Phe (Phenylalanine), K = Lys (Lysine), G = Gly (Glycine), E = Glu (Glutamate), Q = Gln (Glutamine), P = Pro (Proline), R = Arg (Arginine), A = Ala (Alanine)

Based on the aforementioned research, the inventors produced a non-T cell binding peptide which can only bind to DRβ1 molecules and which cannot be recognized by T cell receptors by substituting the amino acids which can bind to T cell receptors and which can stimulate T cell proliferation in CII peptide with Alanine (A) and Glycine (G), and remaining the amino acids which can bind to HLA-DRβ1. The non-T cell binding peptides can specifically bind to HLA-DRβ1, and competitively inhibit the binding of autoantigens to HLA-DRβ1, and thus inhibit HLA-DRβ1 mediated autoimmune responses and inhibit so induced pathologic processes, such as release of inflammatory factors.

Therefore, in the embodiments of the present invention, non-T cell binding peptides and their analogs are provided. The following peptides are preferred: FKGEAGPKGE (SEQ ID NO:1), FKGEQAPKGE (SEQ ID NO:2), FKGEQGAKGE (SEQ ID NO:3), FKGEQGPAGE (SEQ ID NO:4), FKGEQGAAGE (SEQ ID NO:5), FKGEQAGAGE (SEQ ID NO:6), and FKGEGAGAGE (SEQ ID NO:7). These polypeptides can bind to the specific sequence of QKRAA (SEQ ID NO:9) or QRRAA (SEQ ID NO:10) (i.e. Gln-Lys/Arg-Arg-Ala-Ala) in HLA-DRβ1 which is related to the onset of rheumatoid arthritis, and can thereby inhibit T cell activation, and consequently reach the goal of treating rhuematoid arthritis and other autoimmune disease mediated by T cells.

In the embodiments of the present invention, compositions comprising said non-T cell binding peptides or their analogs and pharmaceutically accepted carriers or adjuvants are also provided.

The pharmaceutically accepted carriers or adjuvants include lactose, sucrose, sorbic alcohol, mannitol, potato starch, maize starch or amylopectin, cellulose derivatives, glutin, magnesium stearate, calcium stearate and so on. The compositions can be made in the form of tablet, pill, capsule, syrup, powder, granula or liquor and so on. For example, for oral administration of said pharmaceutical composition, the active compound can be mixed with said pharmaceutically accepted carriers or adjuvants, and then impacted into tablets which can be further coated if necessary.

Liquor may also include other excipients well known in the art. The pharmaceutical compositions can also include some pharmaceutically accepted carriers, such as water, suspension agent, emulsifier and other ingredients.

The content of the non-T cell binding polypeptides or their analogs in the compositions of the present invention are usually 50-200 μg/tablet and optimally, 100 μg/tablet. A person skilled in the art can determine the particular amount of non-T cell binding polypeptides of the present invention to be administered according to the state of illness, body weight and age of patients.

The non-T cell binding peptides or their analogs of the present invention can be administered to arthritis patients by a variety of methods (oral administration, injection and so on).

BRIEF DESCRIPTION OF THE DRAWINGS

FIG. 1: The similarity of tridimensional conformations of five published HLA-DRβ1 binding polypeptides (CII, HSP70, Clip, HA and HB). The five overlapped polypeptides are shown in different colors. The conformations of these peptides are shown from different angles in the left and right figure. From the figure, it can be seen that the conformations of these polypeptides are extremely similar. The left side chains of amino acids at position 1 (P1), position 4 (P4) and position 9 (P9) bind to HLA-DRβ1 and are imbedded into the antigen binding clefts entirely or partially. The side chains of other amino acids stretch to another side or the orientation of TCR which is opposite to HLA-DRβ1 in order to stimulate T cell activation. (Immunity 7:473-81,1997)

FIG. 2: The crystal structure of HLA-DRβ1 binding to CII polypeptide. The side chains at P1, P4 and P9 of CII polypeptide are imbedded into the antigen binding "pocket" (s) of HLA-DRβ1. The polar binding point with high affinity is formed by (positively charged) $Lys_71$ in HLA-DRβ1 and P4 (Glu, negatively charged) (Immunity 7:473-81,1997).

FIG. 3: The comparison of the effects of non-T cell binding peptides and wild type CII polypeptide on T cell activation. Compared with wild type CII peptide, none of polypeptides Mut 267-270, Mut 268-270, Mut 269-270, 269A and 270A has significant effect on T cell activation.

FIG. 4: The inhibition effects of non-T cell binding peptides on T cell activation. While co-incubating non-T cell binding peptides and wild type peptides with T cell activation stimulation systems, the T cell activation effects of wild type DRβ1 binding peptides can be inhibited significantly by non-T cell binding peptides. The higher the concentration of non-T cell binding peptides is, the heavier the inhibition effect is.

FIG. 5: The synovium pathological characters of CIA arthritis models. Incrassation synovium and lymphocye infiltration are found using HE staining. Pannus formation is found in some joints. It is positively correlated between the pathological changes and the ratio of joint swelling.

FIG. 6. The therapeutic effects of non-T cell binding peptide (267A) on Collagen-Induced Arthritis (CIA). On Day 8, 10, 12 and 14, the swelling ratio(s) of right feet and arthritis score(s) of the three treatment groups are all significantly lower than those of the control group (p<0.05 or 0.01). On Day 8 and Day 16 after the treatment, the remission ratio(s) of CIA in the control group are significantly lower than that in the three treatment groups (p<0.05).

FIG. 7. The Inhibition effects of non-T cell binding peptide (267A) on collagen-induced arthritis (CIA) TNFα. The concentration of TNFα in peripheral blood in 100 μg/ml treated group is significantly lower than that of the control group (p<0.05). No significant variety is found while comparing the other two treatment groups with the control group.

The following examples will be used to further illustrate the present invention, rather than limiting the scope of the present invention.

DETAILED DESCRIPTION OF SPECIFIC EMBODIMENTS

EXAMPLE 1

Polypeptide Design and Synthesis

It proves in the research mentioned above [4,5,9-11] that amino acids P267-270 in CII polypeptide mainly bind to T cell receptors and activate T cells. In the experiments of the present invention, firstly, a group of seven non-T cell binding peptides containing a single or multiple amino acid substitutions (CII 267-270) (table 2) were synthesized using solid-phase technique reported by Flechsler et al.[14]. In order to increase the absorption ratio and the bioavailability of these polypeptides and enhance the therapeutic effect, the amino-terminal of each peptide was linked to a myristic acid gene in the process of synthesis to facilitate transportation of the polypeptides into cells. The ten-amino-acid-peptides used in this research all contain four or more hydrophilic residues, such as Lysine (K) and Glutamate (E), and are easy to be dissolved and absorbed. These peptides do not contain methionine (M) and tryptophan (W), which can be degraded easily, nor contains Aspartate (N) from which the amino group or the carboxyl group is prone to be removed. Therefore, the peptides are stable, and it is easy for them to enter into the cells and play a role in disturbing T cell recognition.

TABLE 2

Design of non-T cell binding peptides

| Names of polypeptides | Amino acid position | | | | | | | | | |
|---|---|---|---|---|---|---|---|---|---|---|
| | 263 | 264 | 265 | 266 | 267 | 268 | 269 | 270 | 271 | 272 |
| CII WTM (SEQ ID NO:8) | F | K | G | E | Q | G | P | K | G | E |
| 267A (SEQ ID NO:1) | — | — | — | — | A | — | — | — | — | — |
| 268A (SEQ ID NO:2) | — | — | — | — | — | A | — | — | — | — |
| 269A (SEQ ID NO:3) | — | — | — | — | — | — | A | — | — | — |
| 270A (SEQ ID NO:4) | — | — | — | — | — | — | — | A | — | — |
| Mut 269-270 (SEQ ID NO:5) | — | — | — | — | — | — | A | A | — | — |
| Mut 268-270 (SEQ ID NO:6) | — | — | — | — | — | A | G | A | — | — |
| Mut 267-270 (SEQ ID NO:7) | — | — | — | — | G | A | G | A | — | — |

It has been indicated by research that with substitution of T cell binding amino acids (267-270) with Alanine (A) and/or Glycine (G) respectively, the aforementioned seven non-T cell binding peptides are able to suppress T cell activation. Among them, the significant effects of polypeptide 267A and Mut 267-270 have been demonstrated in cell line tests and rheumatoid arthritis animal models (described later).

EXAMPLE 2

The Inhibition Effects of Non-T Cell Binding Peptides of the Present Invention on T Cell Activation Antigen polypeptides are expressed through antigen presenting cells and activate T cells, resulting in the production of inflammation factors in vivo, and further resulting in the typical pathologic changes of rheumatoid arthritis. In the experiment, the inhibition effects of non-T cell binding peptides on T cell activation were detected by measuring T cell proliferation and Interleukin (IL)-2 level. Two sets of systems of antigen presenting and T cell activation, which are recognized internationally, are used in the research.

| | |
|---|---|
| Antigen presenting cells: | L57.23 cell: recognizing HLA-DR1 antigen (transgened with DR1) |
| | Priess cell: recognizing HLA-DR1/4 (transfected with EBV) |
| T-cells: | 3.19 cell: HLA-DR1-specific T cell clone |
| | 3838 cell: HLA-DR4-specific T cell clone |

Wherein one set of antigen presenting and T cell activation system is composed of L57.23 cell and 3.19 cell, and the other set of system is composed of Priess cell and 3838 cell. By comparing the difference in the effects of said seven non-T cell binding peptides on antigen presenting and T cell activation, non-T cell binding peptides which have significant inhibition effect(s) on T cell activation were screened.

Firstly, the antigen presenting cells, different non-T cell binding peptides (10 μg/ml) and corresponding T cells were added into the reaction system and co-incubated at 37° C. for 48 hours. The supernatant was obtained and added into well-grown IL-2 dependent cells (CTLL). The CTLL cell proliferation was detected by using titrazolium salt method (MTT). Thus the inhibition effects of non-T cell binding peptides on T cell activation were determined.

The results of this research showed that wild type DRβ1 binding peptide was able to stimulate T cell proliferation at a concentration of 400 μg/ml, 200 μg/ml, 80 μg/ml, 40 μg/ml and 20 μg/ml, and high concentration of IL-2 could be detected in the supernatant. However, the stimulation effects of the seven non-T cell binding peptides on T cell activation were significantly weaker and the concentration of IL-2 in the supernatant was significantly lower than that of wild type peptide ($p<0.01$) (FIG. 3). Non-T cell binding peptides can significantly inhibit the T cell activation effects of wild type DRβ1 binding peptides when the non-T cell binding peptides were co-incubated with wild type peptides and T cell activation system. Moreover, the effect of inhibition increased with the increase of concentration of non-T cell binding peptides (FIG. 4). Further tests proved that using non-T cell binding polypeptides with substitution on amino acid 267 to treat collagen-induced arthritis rats, the joint swelling and inflammatory reactions could be significantly alleviated. The above results show that the wild type CII263-272 polypeptide contains the antigen epitope of Collagen type II, and non-T cell binding peptides produced by substituting T cell binding amino acids of CII263-272 can block the recognition of T cell receptors to that polypeptide and thus inhibit T cell activation. All these results suggest that non-T cell binding peptides might lead to a new method to interfere the autoimmune responses mediated by HLA-DR1/DR4.

EXAMPLE 3

The Inhibition Effects of Non-T Cell Binding Peptides of the Present Invention on Experimental Arthritis During the immune responses that lead to arthritis, antigen presenting cells induce T cell activation through antigen(s) and promote T cell proliferation, increase the in vivo cytokine (e.g. TNFα, IL-1) level in animals and thereby lead to typical pathological changes of rheumatoid arthritis. Therefore, the inhibition effects of non-T cell binding peptides on arthritis can be determined by detecting the level of in vivo cytokines in the experimental animals. The therapeutic effects can also be evaluated through a pathological section (slice) from a histological perspective.

In the animal experiment protocol of the present invention, collagen-induced arthritis (CIA) in Wistar rats was induced by bovine CII. The non-T cell binding peptides of the present invention were used to treat the arthritis rats. It was found that polypeptide 267A could significantly suppress arthritis in rats and alleviate the swelling of joints, and shorten the disease course (see the results).

(1) The Establishment of Experimental Arthritis Animal Model(s)

The experimental arthritis model used in the present invention is collagen-induced arthritis (CIA) which is recognized internationally. The experimental animals used were American Wistar rats, which belong to a blocking colony. They were cultured successfully by Wistar Institute of USA in 1907. They are among the species that were introduced into our country earliest and were used most widely. The rats used in this experiment were all cultured in the animal center of People's Hospital, Peking University (SPF degree II). The rats were cultured in the polyacylene cages cushioned by serrago. The lightness/darkness cycle was maintained as 12 h/12 h. The water and food were freely available to the rats. All the rats used in the experiment were male, 8-10 weeks of age, body weight 180±10 g. All the protocols related to animals in the experiment were in accordance with *Chinese Experimental Animal Regulations.*

The bovine type II collagen (catalogue number: C11188) was bought from Sigma Co. Ltd. It was dissolved in acetic acid to make a solution with the final concentration of 8 mg/ml. Then the solution was emulsified with complete Freund's adjuvant (Detroit, USA) of the equal volume. 100 μl of the emulsified solution was injected into the footpad of the right limb of each Wistar rat. The injection dose was 400 μl/rat. Thus the arthritis model of Wistar rats was successfully established.

(2) The Evaluation of Arthritis

The swelling of metatarsophalangeal joints and interphalangeal joints was found on all the rats about 15 days after the induction of arthritis in Wistar rats with CII. A 0-16 scale was used to evaluate the extent of arthritis. Each of the 4 paws was assigned a score using a 0-4 scale, wherein zero=no joint swelling, 1=swelling of one joint, 2=swelling of 2 joints, 3=swelling of 3 joints, and 4=swelling of 4 joints, which is the swelling of the whole paw. Four paws were scored respectively, and these scores were summed up to give a total score. Beginning 2 days after the immunization, the rats were subjected to an inspection every day until the experiment had been finished.

(3) Treatment of Arthritis in Wistar Rats by Non-T Cell Binding Peptide(s)

The arthritis rats were randomly divided into 4 groups from Day 4 to Day 7 after arthritis induced therein. There were 3 treatment groups and one control group. Each group consisted of 10 rats. Non-T cell binding peptide 267A was subcutaneously injected into the base of tail of each rat every 3 days. The peptides were dissolved in sterile distilled water before injection. The concentrations used in the 3 treatment groups were 100 μg/ml, 500 μg/ml and 1000 μg/ml respectively, 100 μl for each rat, and the control group received sterile distilled water only. The volume change of right feet was measured by water-expelling method every day. Using the aforementioned method of arthritis evaluation, the arthritis scores were given every day based on the number of joints with arthritis. The rats were killed 18 days after treatment. The peripheral blood was collected. The serum concentrations of the respective cytokines were detected using ELISA kits of TNFα and IL-2 (JingMei Biotech Co. Ltd, ShenZhen, P.R.C). In the meanwhile, the joints of the right limb were detached, fixed, decalcified, sectioned and subjected to HE staining.

(4) Statistical Analysis was Carried Out Using SPSS Software Package.

(5) Results: the Inhibition Effects of the Non-T Cell Binding Peptides of the Present Invention on Experimental Arthritis.

40 male Wistar rats were subjected to induction of arthritis by bovine collagen type II. As a result, metatarsophalangeal and interphalangeal joint swelling in different degrees appeared in all the rats from Day 14 to Day 17. From Day 4 to Day 7 after the appearance of arthritis, the rats were randomly divided into 4 groups, one of which was the control group, while the other three were treatment groups. There were 10 rats in each group. The polypeptide 267A concentrations used in the 3 groups were 100 µg/ml, 500 µg/ml and 1000 µg/ml respectively. The scores were given based on the numbers of joints with arthritis by using the aforementioned method of arthritis evaluation.

Figure 1:
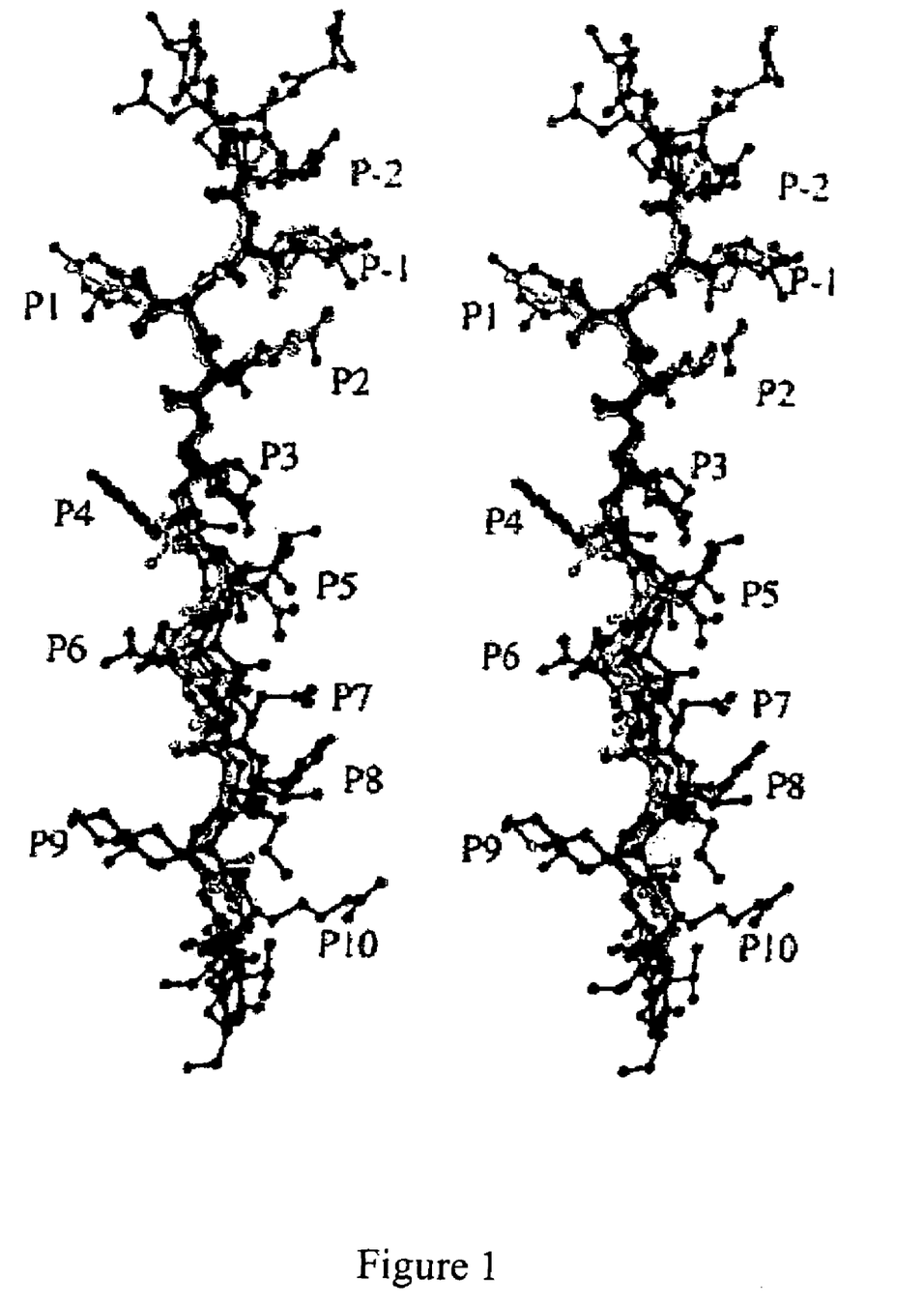
Figure 2:
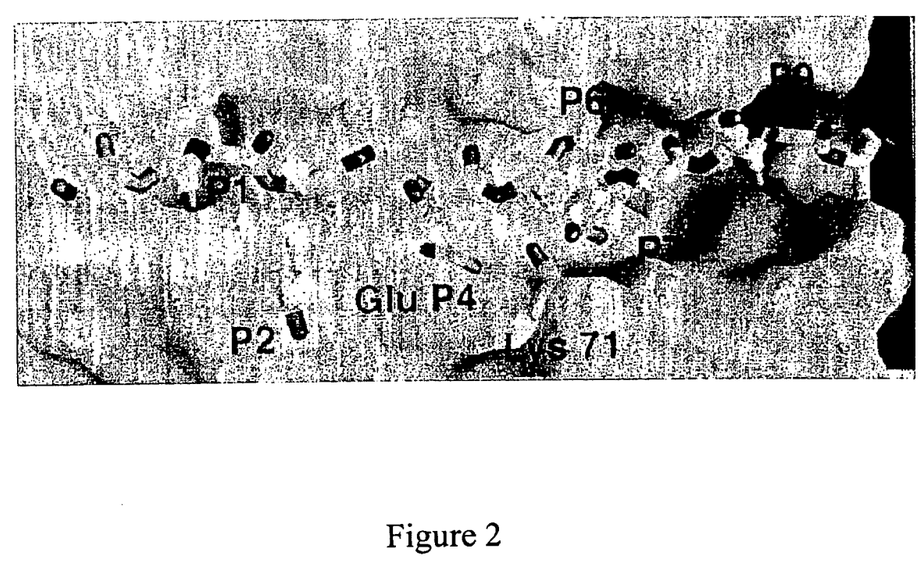
Figure 3:
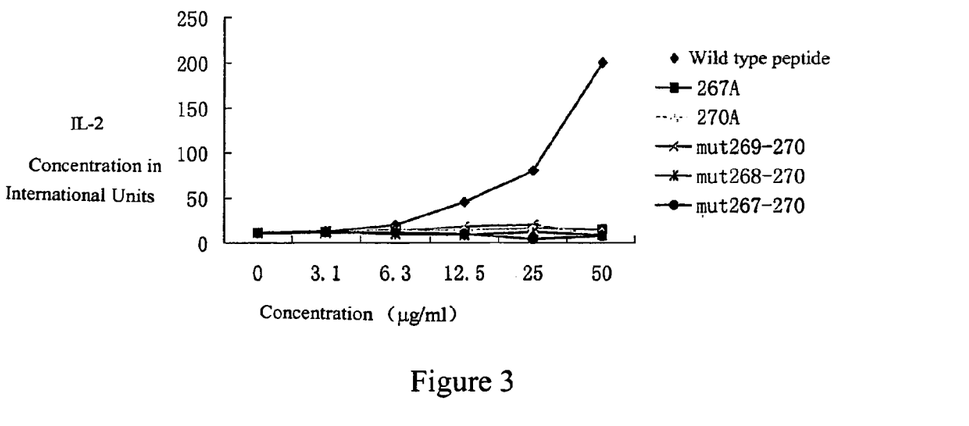
Figure 4:
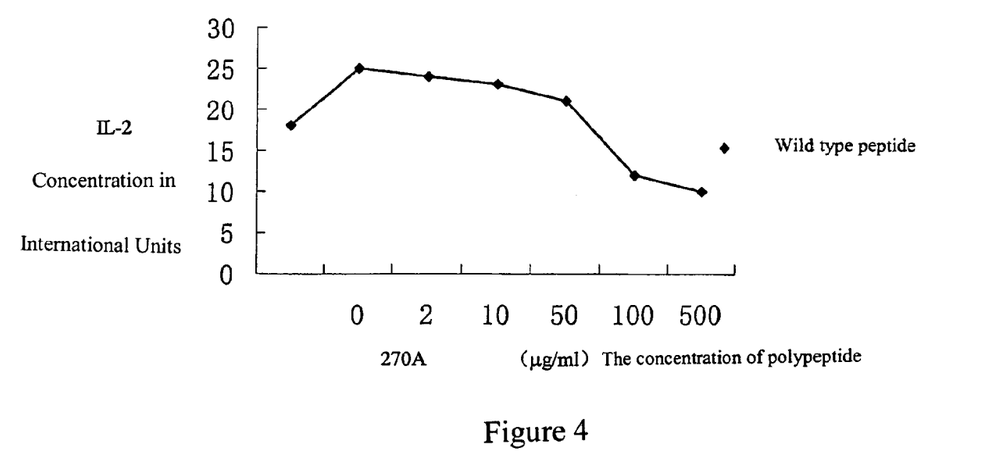
Figure 5:
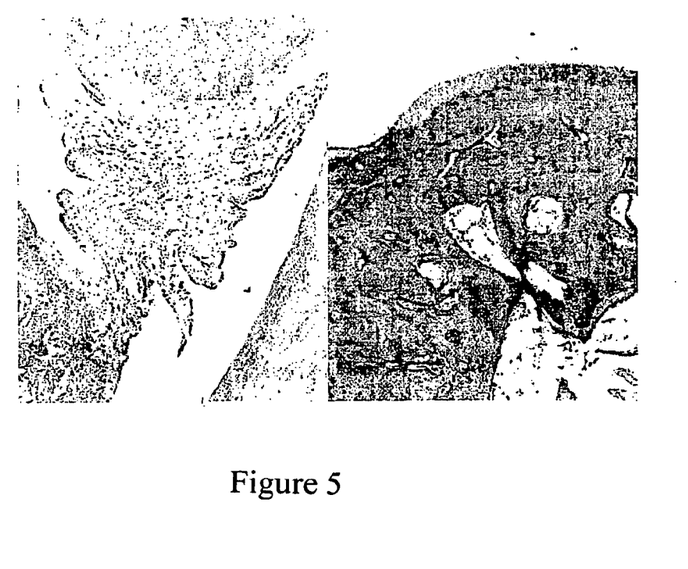

As shown in the results, before the treatment, no significant difference of arthritis scores on right foot swelling ratio and concentration of IL-2 in peripheral blood was observed among the groups. HE staining of all the swollen ankles and metatarsophalangeal joints showed synovial membrane hyperplasia and lymphocyte infiltration in different degrees, and pannus formation was found in some joints (FIG. 5). The pathological changes correlated positively with joint swelling. The swelling of the right feet of rats in the 3 treatment groups was alleviated within the first 2 weeks after treatment, while no significant change on the swelling of the right feet was found in the control group.

Figure 6:
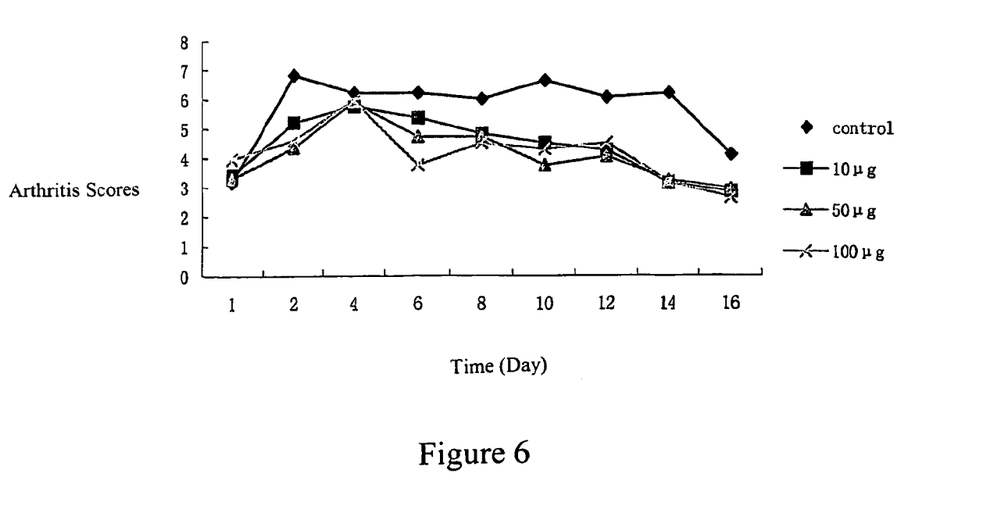
Figure 7:
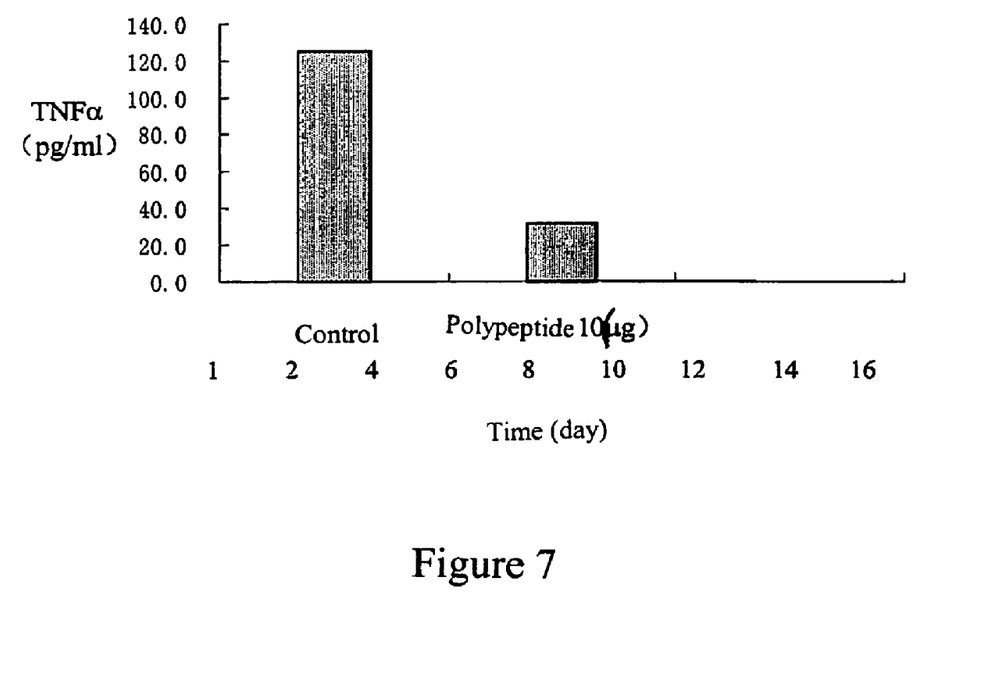

After the treatment of non-T cell binding peptide 267A of the present invention to the rats with arthritis, the arthritis of all the rats in the 3 treatment groups began to be significantly alleviated on Day 4 after the drug administration (FIG. 6, Table 3 as below). The remission ratios of the 3 treatment groups were significantly higher than those of the control group (P<0.05). On Day 8, 10, 12 and 14, both the right foot swelling ratios and the arthritis scores of the 3 treatment groups were significantly lower than those of the control group (P<0.01); no significant difference among the 3 treatment groups was observed. The TNFα concentrations in the peripheral blood of 100 µg/ml treated group were significantly lower than those of the control group (P<0.05, FIG. 7). All the results prove that non-T cell binding peptides can reduce the auto-immune inflammation in the rats with arthritis, inhibit the collagen-induced arthritis, and the peptides might have therapeutic effects on rheumatoid arthritis.

TABLE 3

The changes of right hind foot swelling in rats of different groups

| | Number | Ankle | Toe1 | Toe2 | Toe3 | Toe4 | Toe5 | Hind foot volume (ml) | number of swollen joints | Average |
|---|---|---|---|---|---|---|---|---|---|---|
| control group | 1 | + | + | + | + | + | + | 1.5 | 6 | 6.2 |
| | 2 | − | + | ++ | ++ | ++ | − | 1.4 | 7 | |
| | 3 | + | ++ | ++ | + | ++ | − | 1.5 | 8 | |
| | 5 | + | − | ++ | + | + | + | 1.3 | 6 | |
| | 6 | + | − | + | + | + | ++ | 1.4 | 6 | |
| | 7 | + | − | + | ++ | + | + | 1.3 | 6 | |
| | 8 | + | ++ | − | + | + | + | 1.5 | 6 | |
| | 9 | + | + | + | + | + | + | 1.4 | 7 | |
| | 10 | + | + | + | − | + | − | 1.2 | 4 | |
| 10 mg group | 1 | + | − | − | + | − | − | 1.2 | 2 | 3.15* |
| | 2 | − | + | + | − | + | + | 1.5 | 4 | |
| | 3 | + | + | − | − | − | + | 1.4 | 3 | |
| | 4 | − | − | − | − | + | ++ | 1.3 | 3 | |
| | 5 | + | − | + | − | − | ++ | 1.3 | 4 | |
| | 6 | + | − | + | − | − | − | 1.3 | 2 | |
| | 7 | − | + | − | − | − | − | 1.1 | 1 | |
| | 8 | + | + | ++ | − | + | + | 1.3 | 6 | |
| | 9 | + | − | − | − | − | − | 1.3 | 1 | |
| | 10 | + | ++ | + | − | − | − | 1.2 | 4 | |
| 50 mg group | 1 | + | + | + | − | + | − | 1.4 | 4 | 3.25* |
| | 2 | + | + | − | ++ | + | + | 1.4 | 6 | |
| | 3 | + | + | + | − | + | − | 1.4 | 4 | |
| | 4 | − | + | − | + | ++ | ++ | 1.7 | 6 | |
| | 5 | + | − | − | − | + | − | 1.3 | 2 | |
| | 6 | + | − | − | − | − | − | 1.4 | 1 | |
| | 7 | + | − | − | − | − | − | 1.1 | 1 | |
| | 8 | − | − | + | − | − | − | 1.6 | 1 | |
| | 9 | + | + | − | − | − | + | 1.6 | 3 | |
| | 10 | − | − | − | + | + | + | 1.4 | 3 | |

*The number of swollen joints significantly reduced compared with the control group (p < 0.01).

The applicant also performed the aforementioned experimental research of T cell activation assay and/or CIA models with other non-T cell binding peptides of the present application, including 268A, 269A, 270A, Mut 267-270 and Mut 267-270, and the results achieved were similar to the results of 267A.

REFERENCES

1 Gregersen P. K, et al.: Arthritis Rheum 30: 1250-1213, 1987.
2 Wucherpfennig K W et al.: J Exp Med. 181:1597-1600, 1995.
3 Zhanguo Li et al.: Chinese Journal of Immunology, 2002, 18: 76-78.
4. Li Z G et al.: J Clin Invest (submitted) 2001.
5 Li Z G et at.: Chin Med J 2002.
6 Zhanguo Li et al.: Clinical Chinese Journal of Internal Medicine 2001, 40: 19-21.

7 Zhanguo Li et al.: National Medical Journal of China 2001, 81: 111-113.
8 Zhanguo Li et al.: Clinical Chinese Journal of Rheumatology 2001, 5: 145-147.
9 Stern L J, et al.: Nature 368: 215-221, 1994.
10 Fremont D H et al.: Science 272: 1001-1004, 1996.
11 Jardetzky T S, et al.: Proc. Natl. Acad. Sci. USA93:734-738, 1996.
12 Dessen A, et al.: Immunity 7:473-81,1997.
13 Rosloniec E F, et al: J Exp Med.185: 1113-1122, 1997.
14 Anderson E C, et al: Proc. Natl. Acad. USA 95: 7574-79, 1998.
15 Flechsler I et al.: J Pept Scil (3): 141-200, 1995.

The invention claimed is:

1. A ten-amino acid peptide, which is obtained by substituting one or more amino acids in position No. 5-No. 8 in the amino acid sequence FKGEQGPKGE (SEQ ID NO:8) with alanine and/or glycine.

2. The peptide according to claim 1, wherein the amino acid sequence of the peptide is selected from the group consisting of the following sequences: SEQ ID NO:1, SEQ ID NO:2, SEQ ID NO:3, SEQ ID NO:4, SEQ ID NO:5, SEQ ID NO:6, and SEQ ID NO:7.

3. A pharmaceutical composition comprising:
   (a) the peptide according to claim 1; and
   (b) a pharmaceutically acceptable carrier and/or adjuvant and/or excipient.

4. The pharmaceutical composition according to claim 3, wherein the amino acid sequence of the peptide is selected from the group consisting of the following sequences: SEQ ID NO:1, SEQ ID NO:2, SEQ ID NO:3, SEQ ID NO:4, SEQ ID NO:5, SEQ ID NO:6, and SEQ ID NO:7.

5. A method for treating rheumatoid arthritis in a subject, comprising administering to the subject an effective amount of the peptide according to claim 1.

6. The method according to claim 5, wherein the amino acid sequence of the peptide is selected from the group consisting of the following sequences: SEQ ID NO:1, SEQ ID NO:2, SEQ ID NO:3, SEQ ID NO:4, SEQ ID NO:5, SEQ ID NO:6, and SEQ ID NO:7.

* * * * *

SEQUENCE LISTING

```
<160> NUMBER OF SEQ ID NOS: 7

<210> SEQ ID NO 1
<211> LENGTH: 10
<212> TYPE: PRT
<213> ORGANISM: Artificial sequence
<220> FEATURE:
<223> OTHER INFORMATION: Synthesized

<400> SEQUENCE: 1

Phe Lys Gly Glu Ala Gly Pro Lys Gly Glu
1               5                   10

<210> SEQ ID NO 2
<211> LENGTH: 10
<212> TYPE: PRT
<213> ORGANISM: Artificial sequence
<220> FEATURE:
<223> OTHER INFORMATION: Synthesized

<400> SEQUENCE: 2

Phe Lys Gly Glu Gln Ala Pro Lys Gly Glu
1               5                   10

<210> SEQ ID NO 3
<211> LENGTH: 10
<212> TYPE: PRT
<213> ORGANISM: Artificial sequence
<220> FEATURE:
<223> OTHER INFORMATION: Synthesized

<400> SEQUENCE: 3

Phe Lys Gly Glu Gln Gly Ala Lys Gly Glu
1               5                   10

<210> SEQ ID NO 4
<211> LENGTH: 10
<212> TYPE: PRT
<213> ORGANISM: Artificial sequence
<220> FEATURE:
<223> OTHER INFORMATION: Synthesized

<400> SEQUENCE: 4

Phe Lys Gly Glu Gln Gly Pro Ala Gly Glu
1               5                   10

<210> SEQ ID NO 5
<211> LENGTH: 10
<212> TYPE: PRT
<213> ORGANISM: Artificial sequence
<220> FEATURE:
<223> OTHER INFORMATION: Synthesized

<400> SEQUENCE: 5

Phe Lys Gly Glu Gln Gly Ala Ala Gly Glu
1               5                   10
```

```
<210> SEQ ID NO 6
<211> LENGTH: 10
<212> TYPE: PRT
<213> ORGANISM: Artificial sequence
<220> FEATURE:
<223> OTHER INFORMATION: Synthesized

<400> SEQUENCE: 6

Phe Lys Gly Glu Gln Ala Gly Ala Gly Glu
1               5                   10

<210> SEQ ID NO 7
<211> LENGTH: 10
<212> TYPE: PRT
<213> ORGANISM: Artificial sequence
<220> FEATURE:
<223> OTHER INFORMATION: Synthesized

<400> SEQUENCE: 7

Phe Lys Gly Glu Gly Ala Gly Ala Gly Glu
1               5                   10
```